United States Patent [19]

Martin et al.

[11] Patent Number: 4,496,580

[45] Date of Patent: Jan. 29, 1985

[54] OXOTHIENOBENZOXEPINS

[75] Inventors: Lawrence L. Martin, Lebanon; Linda L. Setescak, Somerville, both of N.J.

[73] Assignee: Hoechst-Roussel Pharmaceuticals Inc., Somerville, N.J.

[21] Appl. No.: 285,897

[22] Filed: Jul. 23, 1981

[51] Int. Cl.³ .................. H61K 31/38; C07D 495/04
[52] U.S. Cl. ................................. 514/443; 549/31; 549/71
[58] Field of Search ............... 549/31, 44; 424/275

[56] References Cited

U.S. PATENT DOCUMENTS

| | | | |
|---|---|---|---|
| 3,639,613 | 2/1972 | Dunn et al. | 549/31 |
| 4,025,640 | 5/1977 | McFadden et al. | 549/31 |
| 4,081,457 | 3/1978 | McFadden et al. | 549/31 |
| 4,211,877 | 7/1980 | Lee | 549/31 |

FOREIGN PATENT DOCUMENTS

| | | | |
|---|---|---|---|
| 1088507 | 4/1958 | Fed. Rep. of Germany | 549/31 |
| 51-136697 | 5/1975 | Japan | 549/31 |
| 52-83591 | 7/1977 | Japan | 549/31 |
| 124777 | 9/1980 | Japan | 549/31 |

OTHER PUBLICATIONS

Chem. Abs., 56, 456i.
Yoshioka, et al., J. Med. Chem., 21, 633 (1978).
Aultz, et al., J. Med. Chem., 20, 1499 (1977).
Aultz, et al., J. Med. Chem., 20, 66 (1977).
Spinelli, et al., J. Chem., Soc., Perkin 2, 1972 (12), 1866.
Bourguignon, et al., C. R. Aiod. Scie. Paris, Sec. C 1970, 270 (5), 494-570.
Reichel, et al., Z. Chem., III, 190 (1963).
Baird, et al., JACS, 84, 788 (1962).

Primary Examiner—Henry R. Jiles
Attorney, Agent, or Firm—Raymond R. Wittekind

[57] ABSTRACT

The invention relates to oxothienobenzoxepin compounds of the formula

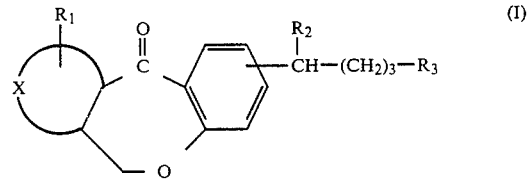

where X together with the carbon atoms to which it is attached is a thiophene ring;
$R_1$ is hydrogen, a straight or branched chain alkyl group having 1 to 5 carbon atoms or a halogen atom;
$R_2$ is hydrogen or a straight chain alkyl group having 1 to 5 carbon atoms; and
$R_3$ is hydroxyl or

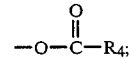

where $R_4$ is a straight chain or branched chain alkyl group having 1 to 10 carbon atoms, a phenyl group or a trifluoromethyl group.

Methods for preparing the compounds and their use as antiinflammatory and analgesic agents are provided.

51 Claims, No Drawings

OXOTHIENOBENZOXEPINS

This invention relates to oxothienobenzoxepin derivatives, methods for their preparation and their use as antiinflammatory and analgesic agents.

A group of oxothienobenzoxepin compounds useful as antiinflammatory and analgesic agents is disclosed by Arthur R. McFadden et al in U.S. Pat. No. 4,025,640. The compounds are represented by the formula

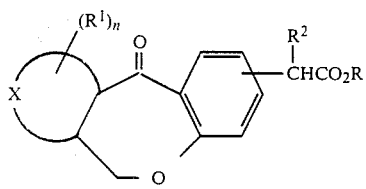

wherein X, together with the carbon atoms to which it is attached, is a 5 or 6-membered heteroaryl ring structure containing from 1 to 2 oxygen, nitrogen or sulfur atoms; R is hydrogen or straight or branched chain alkyl of from 1 to 5 carbon atoms; $R^1$ is hydrogen or lower alkyl of 1 to 4 carbon atoms, $R^2$ is hydrogen or methyl; and n is the integer 1, 2 or 3. When X together with the carbon atoms to which it is attached is a thiophene ring and when R, $R^1$ and $R^2$ are each hydrogen, the resulting compounds are oxothienobenzoxepin acetic acids.

Another group of oxothienobenzoxepin compounds has now been discovered. These compounds are also useful as antiinflammatory and analgesic agents. In addition, these new compounds exhibit longer duration of action and lower ulcerogenicity than the oxothienobenzoxepin acetic acids and derivatives disclosed in U.S. Pat. No. 4,025,640.

More particularly, this invention provides compounds of the formula

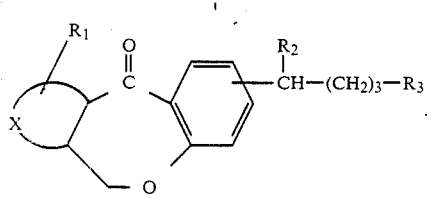

The substituent X together with the carbon atoms to which it is attached is a thiophene ring. The substituent $R_1$ is hydrogen, a straight or branched chain alkyl group having 1 to 5 carbon atoms or a halogen atom, preferably bromine; $R_2$ is hydrogen or a straight chain alkyl group having 1 to 5 carbon atoms; and $R_3$ is hydroxyl or

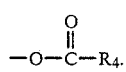

The substutuent $R_4$ is a straight or branched chain alkyl group having 1 to 10 carbon atoms, a phenyl group or a trifluoromethyl group.

This invention also provides a method for preparing compounds of the following formula:

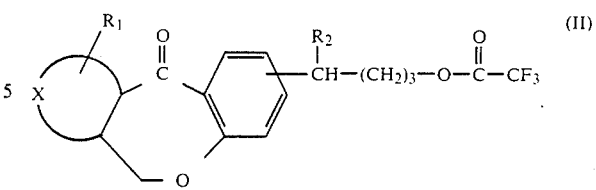

The substituent X together with the carbon atoms to which it is attached is a thiophene ring; $R_1$ is hydrogen, a straight or branched chain alkyl group having 1 to 5 carbon atoms or a halogen atom; and $R_2$ is hydrogen or a straight chain alkyl group having 1 to 5 carbon atoms. The method comprises reacting a compound of the formula

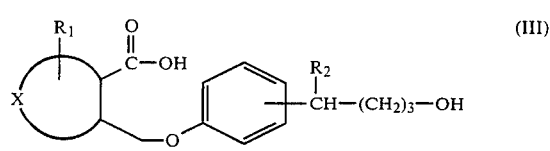

where $R_1$ and $R_2$ correspond to $R_1$ and $R_2$ in formula (II), with trifluoroacetic anhydride in solution at a temperature up to the reflux temperature of the reaction mixture.

In addition, this invention provides a method for preparing a compound of the formula:

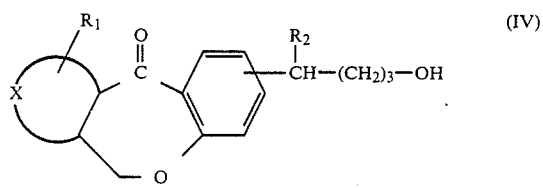

The method comprises hydrolyzing a compound of the formula

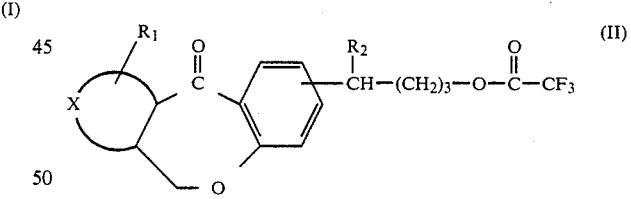

in acidic solution at a temperature up to the reflux temperature of the solvent employed in the solution. In formula (IV) and formula (II), X together with the carbon atoms to which it is attached is a thiophene ring; $R_1$ is hydrogen, a straight chain or branched chain alkyl group having 1 to 5 carbon atoms; and $R_2$ is hydrogen or a straight chain alkyl group having 1 to 5 carbon atoms.

Further, this invention provides a method of alleviating pain in a mammal by administering to a mammal a pain-alleviating effective amount of a compound of formula (I) above.

Stll futher, this invention provides a method of alleviating inflammation in a mammal by administering to a mammal an inflammation-alleviating effective amount of a compound of formula (I) above.

Finally, this invention provides a pharmaceutical composition comprising a compound of the invention and a pharmaceutically acceptable carrier therefor.

The compounds of this invention are represented generally by the foregoing formulae. Where the term alkyl is used in defining the substituents on these compounds, it is to be understood that the alkyl group is acyclic without unsaturation. Straight chain alkyl groups are preferred. It will also be understood that the group of compounds defined by formula (I) includes oxothieno[3,2-c]benzoxepins of the formula

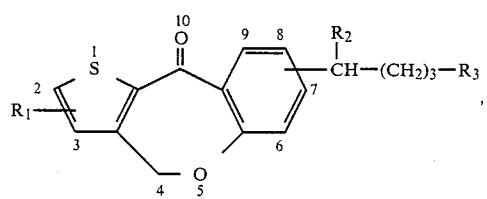
(IA)

where the $-\overset{R_2}{\underset{|}{CH}}-(CH_2)_3-R_3$ moiety is in the 7- or 8-position;
oxothieno[3,4-c]benzoxepins of the formula

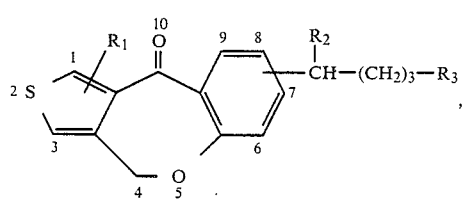
(IB)

where the $-\overset{R_2}{\underset{|}{CH}}-(CH_2)_3-R_3$ moiety is in the 7- or 8-position; and oxothieno[2,3-c]benzoxepins of the formula

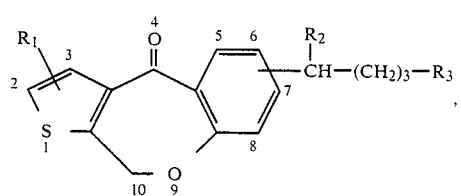
(IC)

where the $-\overset{R_2}{\underset{|}{CH}}-(CH_2)_3-R_3$ moiety is in the 6- or 7-position, and $R_1$, $R_2$ and $R_3$ corresponds to the definition of $R_1$, $R_2$ and $R_3$, respecticely, in formula (I). Among the preferred compounds of the invention are oxothienobenzoxepins in which $R_1$ is hydrogen and $R_2$ is hydrogen or a methyl group. When $R_4$ is an alkyl group, it is preferred that the alkyl group contain from 1 to 5 carbon atoms.

Another group of preferred compounds of this invention are compounds of formula (IA), where $R_1$ is hydrogen, a straight or branched chain alkyl group having 1 to 5 carbon atoms, $R_2$ is hydrogen or a straight chain alkyl group having 1 to 5 carbon atoms and $R_3$ is —OH or

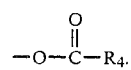

Particularly preferred are such compounds wherein $R_1$ and $R_2$ are each hydrogen.

The compounds of the present invention can be prepared in the following manner. The substituents $R_1$, $R_2$ and $R_3$ are as defined in connection with formula (I) unless otherwise indicated.

An alkyl thiophene ester of the formula

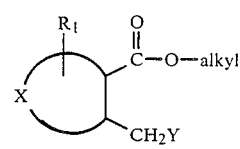
(V)

where X together with the carbon atoms to which it is attached is a thiophene ring, alkyl is a straight chain or a branched alkyl group having 1 to 5 carbon atoms and Y is halogen, preferably bromine, is allowed to react with a m- or p-hydroxyphenyl alkanol of the formula

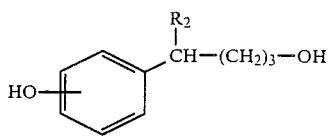
(VI)

to form an ester of the formula

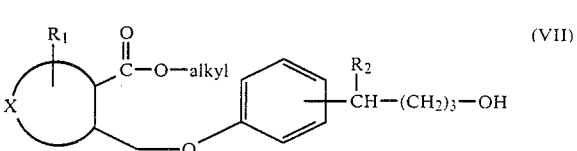
(VII)

For example, the oxothieno[3,2-c]benzoxepins of formula (IA) above can be prepared by reacting an alkyl thiophene ester of the formula

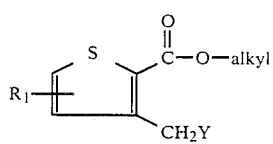
(VIII)

with a m- or p-hydroxyphenyl of the formula

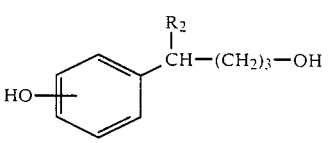
(IX)

to form an ester of the formula

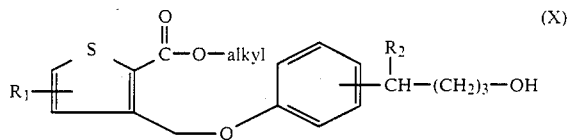

The reaction can be carried out in the presence of a solvent, such as acetone, butanone, ethanol or dimethylformamide. An acid scavenger, such as potassium or sodium ethoxide, is preferably employed. A reaction initiator, such as potassium or sodium iodide, is optional. The reaction is conveniently carried out at a temperature of about ambient temperature to the boiling point of the solvent for a few minutes to about 72 hours to provide a compounding of formula (VII). The resulting compound can be separated from the reaction mixture and purified using well-known techniques.

The halogenated thiophene of formula (V) above can be prepared using conventional techniques. For example, a bromomethyl thiophene ester can be formed by esterifying a substituted or unsubstituted methyl thiophene carboxylic acid with an alkanol to provide the alkyl group in the compound of formula (V), and then brominating the resulting ester with N-bromosuccinimide. Substituted methyl thiophene carboxylic acids and methods for their preparation are known in the art. See, for example, U.S. Pat. No. 3,639,613, German Offenlegungsschrift 1,088,507, and D. Spinelli et al, J. Chem. Soc., Perkin 2 1972 (12), 1866.

Another method that can be employed for selective bromination of the methyl group adjacent to the ester moiety in formula (V) involves a procedure analogous to a prior art method described generally in L. Reichel and W. Hempel, Z, Chem., (III, 190 (1963). This procedure employs a thienofuranone and phosphorus tribromide and bromine as reactants. The reaction involves simultaneous opening of the furanone ring and bromination of the methyl group on the resulting thiophene. Unsubstituted thienofuranones and their method of preparation are disclosed by J. Bourguignon et al, C. R. Acad. Sci. Paris, Ser. C 1970, 270 (5), 494-70. Alkyl substituted thienofuranones can be prepared by conventional techniques. For example, a 2-alkyl-substituted thiophene containing a reactive 4-bromine substituent can be reacted with n-butyllithium and formaldehyde to form a hydroxyalkyl-substituted thiophene-lithio intermediate. Additional treatment with n-butyllithium and with dry ice followed by aqueous quenching affords a 5-alkyl-3-hydroxymethyl thiophene-2-carboxylic acid, which can then be cyclized to form the alkyl-substituted thienofuranone.

The m- or p-hydroxyphenyl alkanol can also be prepared using conventional techniques. For example, a m- or p-methoxyphenylbutyric acid can be reacted at reflux temperature with hydrogen bromide to form a m or p-hydroxyphenylbutyric acid. This acid can then be reacted with borane in tetrahydrofuran to form m- or p-hydroxyphenylbutanol. This latter compound is reported in JACS, 84, 788 (1962).

The ester of formula (VII) is saponified to form the corresponding carboxylic acid. The saponification reaction can be carried out according to conventional techniques. For example, the ester of formula (VII) can be reacted with a base, such as sodium or potassium hydroxide, in a solvent, such as aqueous ethanol or water. Typically, reaction can be carried out at a temperature of from about ambient temperature to the boiling point of the solvent for a period of about 15 minutes to about 24 hours.

The carboxylic acid formed by the saponification of the ester of formula (VII) is then cyclized by a method that will not interfere with the hydroxyl group on the side chain of the phenyl group or by a method in which the hydroxyl group is converted to another moiety that can be readily converted back to the hydroxyl group. One method involves acylating the carboxylic acid to convert the alcohol hydroxyl group to an ester, then cyclizing the acid, such as by treatment with a dehydrating agent, or by converting the carboxylic acid group of the acylated derivative to an acid chloride by reaction with thionyl chloride followed by cyclizaton using aluminum chloride. The acylaton can be carried out using acyl halides or acid anhydrides under well-known reaction conditions to form esters.

A preferred method for preparing compounds in which $R_3$-is

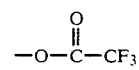

involves reacting a compound of formula (III) with trifluoroacetic anhydride. This reaction is conveniently carried out with about 2 to about 2.5 equivalents of the trifluoroacetic anhydride. Preferably, the trifluoroacetic anhydride is employed in about 15% stochiometric excess. The cyclizaton reaction can be carried out in a suitable solvent, such as dichloromethane or chloroform, at a temperature from about ambient temperature to the reflux temperature of the solvent. The reaction is conducted until substantially complete. This will take about 1 to about 8 hours, typically about 2 hours. The compound of formula (II) can be separated from the reaction mixture and purified according to conventional techniques.

This invention also includes compounds of the following formula:

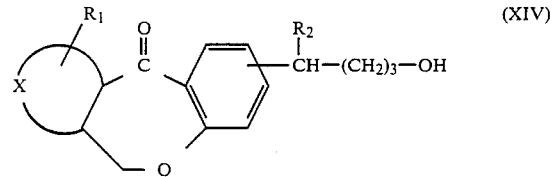

These compounds can be prepared by hydrolyzing compounds of formula (II) under acidic conditions. A strong mineral acid, such as sulphuric acid or hydrochloric acid, is suitable for this hydrolysis reaction. The acid of choice is hydrochloric acid. This reaction can be carried out by dissolving the reactants in a suitable solvent, such as acetone, methyl ethyl ketone or an aqueous alcohol, such as aqueous methanol, ethanol or propanol. The preferred solvent is acetone. The reaction is typically conducted at an elevated temperature, preferably the reflux temperature of the solvent. The reaction is carried out until substantial completion, which can be conveniently determined by chromatographic techniques. Typically, the reaction time will be about 4 to about 24 hours. The resulting oxothienobenzoxepin compounds can be separated from the reaction mixture and purified using well-known techniques. Compounds of formula (XIV) can be readily converted to esters by acylation with acyl halides or acid anhydrides using standard reaction conditions.

Examples of some of the compounds of the invention are:

4-(4,10-dihydro-10-oxothieneo[3,2-c][1]benzoxepin-8-yl)-butyl butyrate;
4-(4,10-dihydro-10-oxothieno[3,2-c][1]benzoxepin-8-yl)-butyl hexanoate;
4-(4,10-dihydro-10-oxothieno[3,2-c][1]benzoxepin-8-yl)butyl 2,2-dimethylpropionate;
4-(4,10-dihydro-10-oxothieno[3,2-c][1]benzoxepin-8-yl)butyl benzoate;
4-(4,10-dihydro-10-oxothieno[3,2-c][1]benzoxepin-8-yl)pentanol;
4-(4,10-dihydro-10-oxothieno[3,2-c][1]benzoxepin-8-yl)pentyl butyrate;
4-(4,10-dihydro-10-oxothieno[3,2-c][1]benzoxepin-7-yl)butanol;
4-(4,10-dihydro-10-oxothieno[3,2-c][1]benzoxepin-7-yl)butyl acetate;
4-(4,10-dihydro-10-oxothieno[3,2-c][1]benzoxepin-7-yl)pentanol;
4-(4,10-dihydro-10-oxothieno[3,4-c][1]benzoxepin-8-yl)butanol;
4-(4,10-dihydro-10-oxothieno[3,4-c][1]benzoxepin-8-yl)butyl acetate;
4-(4,10-dihydro-10-oxothieno[3,4-c][1]benzoxepin-8-yl)pentanol;
4-(4,10-dihydro-10-oxothieno[3,4-c][1]benzoxepin-7-yl)butanol;
4-(4,10-dihydro-10-oxothieno[2,3-c][1]benzoxepin-6-yl)butanol;
4-(4,10-dihydro-10-oxothieno[2,3-c][1]benzoxepin-6-yl)butyl acetate;
4-(4,10-dihydro-10-oxothieno[2,3-c][1]benzoxepin-6-yl)pentanol;
4-(4,10-dihydro-10-oxothieno[2,3-c][1]benzoxepin-7-yl)butanol;
4-(4,10-dihydro-2-methyl-10-oxothieno[3,2-c][1]benzoxepin-8-yl)butanol; and
4-(2-bromo-4,10-dihydro-10-oxothieno[3,2-c][1]benzoxepin-8-yl)butanol.

The compounds of the present invention are useful as systemic antiinflammatory agents due to their ability to suppress inflammation in mammals. The activity of the compounds is demonstrated in the carrageenan-induced rat paw edema antiinflammatory assay. (The carrageenan-induced rat paw edema test is hereinafter referred to as CPE).

The compounds of the present invention are also useful as analgesic agents due to their ability to alleviate pain in mammals. This activity of the compounds is demonstrated in the 2-phenyl-1,4-benzoquinone-induced writhing test in mice. (The phenylquinone-induced writhing test is hereinafter referred to as PQW).

The compounds of the present invention also exhibit surprisingly low ulcerogenic activity. (The ulcerogenic ativity test is hereafter referred to as GI).

The CPE, PQW and GI test methods are reported at J. Med. Chem., 20, 66, 69 (1977). These tests have been used to compare the compounds of the present invention with related compounds disclosed in U.S. Pat. No. 4,025,640. The results are reported in the following Table. Compounds 1 and 2 in the following Table are compounds of the patent. Compounds 3 and 4 are compounds of the present invention.

TABLE

[Structure: thieno-benzoxepin with substituents $R_1$, $R_2$, and side chain $-CH(R_2)-(CH_2)_n-R_3$]

| Compound | $R_1$ | $R_2$ | $R_3$ | n | $ED_{50}$ mg/kg of body weight PQW | $ED_{50}$ mg/kg of body weight CPE | $ID_{50}$ mg/kg of body weight GI |
|---|---|---|---|---|---|---|---|
| 1 | H | H | —COOH | 0 | 4.5 | 3.4 | 33.7 |
| 2 | H | H | $-\text{C}(=\text{O})-\text{O}-\text{CH}(CH_3)_2$ | 0 | 13.7 | 1.6 | 21.6 |
| 3 | H | H | —OH | 3 | 7.4 | 8.6 | >400 |
| 4 | H | H | $-\text{O}-\text{C}(=\text{O})-CF_3$ | 3 | 9.1 | 6.5 | ≈300 |

The data in the Table confirm that compounds 3 and 4 of the invention exhibit activity in the CPE and PQW tests; that is, they are useful as antiinflammatory and analgesic agents. Surprisingly, compounds 3 and 4 exhibit a very low incidence of ulcers in test animals at very high dosage levels.

Effective amounts of the compounds of the present invention may be administered to a subject by one of various methods, for example, as solutions or suspensions, and in some cases intravenously in the form of sterile solutions.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain as the active ingredient, at least about 0.5% by weight of the compounds of the invention. The amount of active ingredient may be varied depending upon the particular form and may conveniently be between about 4 and about 70% by weight of a dosage unit. The amount of the compound present in such compositions is such that a suitable dosage will be obtained. Preferred compositions and preparations according to the present invention are prepared so that an oral dosage unit form contains between about 10 and about 500 milligrams of the compounds of the invention.

The tablets, pills, capsules, troches and the like may also contain the following adjuvants: binder, such as microcrystalline cellulose, gum tragacanth or gelatin; an excipient, such as starch or lactose; a disintegrating agent, such as alginic acid, Primogel, corn starch and the like; a lubricant, such as magnesium stearate or Sterotex; a glidant, such as colloidal silicon dioxide; a sweetening agent, such as sucrose or saccharine; or a flavoring agent, such as peppermint, methyl salicylate or orange flavoring. When the dosage unit form is a capsule, it may contain, in addition to materials of the above type, a liquid carrier, such as a fatty oil. Other dosage unit forms may contain other various materials that modify the physical form of the dosage unit, for example, as coatings. Thus, tablets or pills may be coated with sugar, shellac or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic adminstration, the compounds of the present invention may be incorporated into a solution or suspension. These preparations should contain as active ingredient, at least about 0.1% by weight of the compounds of the invention. Typically, the amount of active ingredient will be between about 0.5 and about 30% by weight of a dosage unit. The amount of the inventive compound present in such compositions is such that a suitable dosage will be obtained. Preferred compositions and preparations according to the present invention are prepared so that a parenteral dosage unit contains between about 0.5 and about 100 milligrams of the compounds of the invention.

The solutions or suspensions may also include the following adjuvants: a sterile diluent, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampules, disposable syringes or multiple dose vials made of glass or plastic.

This invention will now be described in greater detail in the following Examples, in which all parts, proportions, percentages and ratios are by weight unless otherwise indicated.

In view of the amendments to the Manual of Patent Examining Procedure, including Sections 608.01(p); 707.07(1); 2004; 2012 dated January, 1981 and received on or about the week of Sept. 14, 1981, Examples 1–5 of the specification are to be read as if they were expressed in the past tense since they are examples which have actually been carried out.

EXAMPLE 1

3-[4-(1-Hydroxybutyl)phenoxymethyl]-2-thiophenecarboxylic acid methyl ester

A stirred mixture of 3.32 g (0.02 mol) of 4-(4-hydroxyphenyl)-1-butanol, 11.06 g (0.08 mol) of anhydrous $K_2CO_3$, 0.2 g of KI, 4.70 g (0.02 mol) of 3-bromomethyl-2-thiophenecarboxylic acid methyl ester and 100 ml of 2-butanone was heated 24 hours under reflux. The mixture was vacuum filtered and the filtrate was concentrated to an oil which crystallized. A solution of the material and 70 ml of $CH_2Cl_2$ was washed with 10% NaOH, dried ($Na_2SO_4$) and concentrated to an oil which crystallized on trituration with the hexane. The crude material (6.0 g) was extracted with hot (55° C.) cyclohexane (400 ml) to afford 2.15 g (33.6%) of colorless crystals, m.p. 67°–68.5° C. The material appeared pure by TLC (silica gel, ethylacetate, $R_f=0.58$; 20% methanol/toluene, $R_f=0.41$) and the IR (CHCl$_3$), $^1$H-NMR (CDCl$_3$) and MS (M$^+$, 320) were consistent with structure.

ANALYSIS: Calculated for $C_{17}H_{20}O_4S$: 63.73% C; 6.29% H; Found: 63.45% C; 6.30% H.

EXAMPLE 2

3-[4-(1-Hydroxybutyl)phenoxymethyl]-2-thiophenecarboxylic acid

A stirred solution of 30.3 g (0.54 mol) of KOH, 30 ml of water, 17.26 g (0.054 mol) of crude 3-[4-(1-hydroxybutyl)phenoxy]methyl-2-thiophenecarboxylic acid methyl ester and 200 ml of 95% ethanol was heated under reflux. This layer analysis (silica gel, ethyl acetate) indicated the hydrolysis was complete after three hours. The ethanol was removed on a rotary evaporator and the residual syrup was diluted with 200 ml of water and extracted with 100 ml of ether. The aqueous phase was acidified with 50 ml of concentrated hydrochloric acid and with ice water cooling. A yellow solid separated and was collected by vacuum filtration. Thorough washing with water and drying in vacuo at 40° C. over NaOH pellets afforded 9.33 g of yellow solid. Recrystallization from 20 ml of 95% ethanol afforded 5.52 g (31.9) of cream colored material, m.p. 144.5°–146° C. The material appeared pure by TLC (silica gel, acetic acid, $R_f=0.76$; alumina, dimethylformamide, $R_f=0.17$) and the IR (KBr), $^1$H-NMR (DMSO-d$_6$) and MS (M$^+$,306) were consistent with structure.

ANALYSIS: Calculated for $C_{16}H_{18}O_4S$: 62.73% C; 5.92% H; Found: 62.83% C; 5.91% H.

EXAMPLE 3

4-(4,10-Dihydro-10-oxothieno[3,2-c][1]benzoxepin-8-yl)butyl trifluoroacetate

A stirred suspension of 14.33 g (0.0468 mol) of 3-[4-(1-hydroxybutyl)phenoxy]methyl-2-thiophenecarboxylic acid and 150 ml of anhydrous $CH_2Cl_2$ was treated with one portion of trifluoroacetic anhydride (22.60 g, 0.107 mol). The suspended material rapidly dissolved and the stirred solution was heated under reflux for four hours. After standing two days at ambient temperature, the reaction was quenched with water (70 ml) and washed with 50 ml of 5% NaHCO$_3$ solution. The dried (Na$_2$SO$_4$) organic phase was concentrated to an oil, which was further dried by azeotropic distillation of toluene. The oil was dissolved in approximately 15 ml of isopropanol, seeded with product previously prepared on a smaller scale, and stirred until a thick crystalline mass formed. The mass was triturated with isopropanol, followed by vacuum filtration. The filter cake was dried in vacuo at 40° C. to afford 15.08 g (83.8%) of almost colorless crystals, m.p. 65.5°–67° C. The material appeared pure by TLC (silica gel, ethyl acetate, $R_f=0.70$; dichloromethane, $R_f=0.51$) and the IR (KBr), $^1$H-NMR (CDCl$_3$) and MS (M$^+$,384) were consistent with structure.

ANALYSIS: Calculated for $C_{18}H_{15}F_3O_4S$: 56.25% C; 3.93% H; Found: 56.36% C; 3.94% H.

EXAMPLE 4

4-(4,10-Dihydro-10-oxothieno[3,2-c][1]benzoxepin-8-yl)butanol

A stirred solution of 11.42 g (0.0297 mol) of 4-(4,10-dihydro-10-oxothieno[3,2-c][1]benoxepin-8-yl)butyl trifluoroacetate, 480 ml of acetone and 250 ml of 5% hydrochloric acid was heated 20.5 hours under reflux. The cooled solution was concentrated to remove the acetone and the residual biphasic mixture was extracted with ether. The organic phase was washed with 5% NaHCO$_3$, dried (Na$_2$SO$_4$), filtered and concentrated to turbid oil. The oil was subjected to azeotropic distillation with toluene to afford a clear amber oil (9.82 g). A solution of the oil and 20 ml of warm toluene was diluted to the cloud point with cyclohexane, seeded with crystals obtained from a small scale trial recrystallization and stirred. More cyclohexane was added and the resulting mixture was stirred several minutes until solidification was complete. The mixture was allowed to stand overnight at ambient temperature. The material was isolated by vacuum filtration, washed with cyclohexane and dried in vacuo (pump) at ambient temperature to afford 7.73 g (90.2%) of a colorless waxy solid, m.p. 52°–54° C. The material appeared pure by TLC (silica gel, ethyl acetate, R$_f$=0.49; acetonitrile, R$_f$=0.71) and the IR (KBr), $^1$H-NMR (CDCl$_3$) and MS (MH+,289) were consistent with structure.

ELEMENTAL ANALYSIS: Calculated for C$_{16}$H$_{16}$O$_3$S: 66.64% C; 5.59% H; Found: 66.49% C; 5.51% H.

EXAMPLE 5

4-(4,10-Dihydro-10-oxothieno[3,2-c][1]benzoxepin-8-yl)butyl acetate

A stirred solution of 4-(4,10-dihydro-10-oxothieno[3,2-c][1]benzoxepin-8-yl)butanol (8.07 g, 0.028 mol) and sieve-dried pyridine (25 ml) was treated over 0.5 min. with acetic anhydride (8.58 g, 0.084 mol). The solution was stirred for 165 min. at ambient temperature and was then heated on a steam bath for 15 minutes. The hot solution was decanted into water (150 ml) (lower phase yellow oil separated), and the mixture was extracted with dichloromethane (70 ml). The organic phase was washed with 5% hydrochloric acid, water and 5% sodium bicarbonate. The dried (Na$_2$SO$_4$) organic phase was concentrated to an oil, which was further dried by azeotropic distillation of toluene. A small portion of the oil was triturated on a watch glass to afford seed crystals. The main portion of the oil was triturated with hexane and seeded to afford a crystalline solid (8.08 g, 87.3%), m.p. 53.5°–55° C. The material appeared pure by TLC (silica gel, CH$_2$Cl$_2$, R$_f$=0.18; ethyl acetate, R$_f$=0.63) and the IR (CHCl$_3$), $^1$H-NMR (CDCl$_3$) and MS (M+,330) were consistent with structure.

ELEMENTAL ANALYSIS: Calculated for C$_{18}$H$_{18}$O$_4$S: 65.44% C; 5.49% H; Found: 65.45% C; 5.49% H.

What is claimed is:

1. A compound of the formula

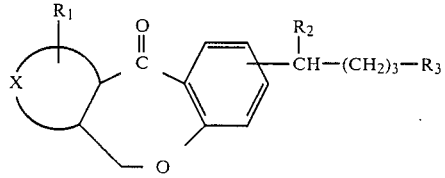

(I)

where X together with the carbon atoms to which it is attached is a thiophene ring;
R$_1$ is hydrogen, a straight or branched chain alkyl group having 1 to 5 carbon atoms or a halogen atom;
R$_2$ is hydrogen or a straight chain alkyl group having 1 to 5 carbon atoms; and
R$_3$ is hydroxyl or

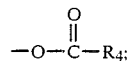

where R$_4$ is a straight chain or branched chain alkyl group having 1 to 10 carbon atoms, a phenyl group or a trifluoromethyl group.

2. A compound according to claim 1 wherein R$_1$ is chlorine or bromine.

3. A compound according to claim 1 wherein R$_2$ is hydrogen or a methyl group.

4. A compound according to claim 1 wherein R$_4$ is a straight or branched chain alkyl group having 1 to 5 carbon atoms.

5. A compound according to claim 1 wherein R$_4$ is a trifluoromethyl group.

6. A compound according to claim 1 wherein R$_3$ is hydroxyl.

7. The compound according to claim 1 which is 3-[4-(1-hydroxybutyl)phenoxymethyl]-2-thiophene carboxylic acid methyl ester.

8. A compound according to claim 1 which is 3[4-(1-hydroxybutyl)phenoxy]methyl-2-thiophene carboxylic acid.

9. A compound according to claim 1 which is 4-(4,10-dihydro-10-oxothieno [3,2-c] [1] benzoxepin-8-yl)-butyl trifluoroacetate.

10. A compound according to claim 1 which is 4-(4,10-dihydro-10-oxothieno [3,2-c] [1] benzoxepin-8-yl)-butanol.

11. A compound according to claim 1 which is 4-(4,10-dihydro-10-oxothieno [3,2-c] [1] benzoxepin-8-yl)-butyl acetate.

12. A compound of the formula

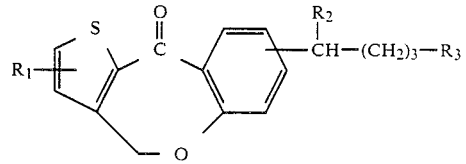

where R$_1$ is hydrogen and a straight chain alkyl group having 1 to 5 carbon atoms, R$_2$ is hydrogen and a straight chain alkyl group having 1 to 5 carbon atoms, and R$_3$ is —OH or

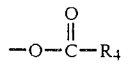

and R$_4$ is a straight chain or branched chain alkyl group having 1 to 10 carbon atoms, a phenyl group or a trifluoromethyl group.

13. A compound according to claim 12 which comprises

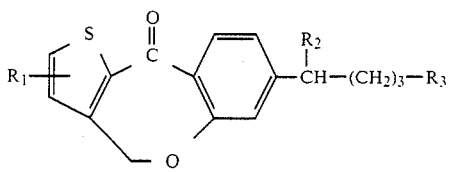

, where $R_1$, $R_2$, $R_3$ and $R_4$ are as defined.

14. A compound according to claim 12 which comprises

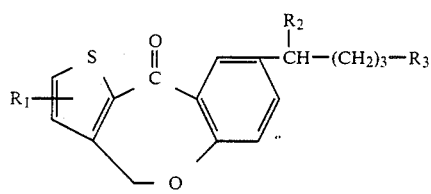

, where $R_1$, $R_2$, $R_3$ and $R_4$ are as defined.

15. A compound according to claims 12, 13 and 14 wherein $R_3$

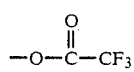

or OH.

16. A compound according to claims 12, 13 or 14 wherein $R_1$ and $R_2$ are each hydrogen.

17. A compound according to claims 12, 13 or 14 wherein $R_4$ is a straight or branched chain alkyl group having 1 to 5 carbon atoms.

18. A compound according to claim 17 wherein $R_1$ and $R_2$ are each hydrogen.

19. A method for preparing a compound of the formula

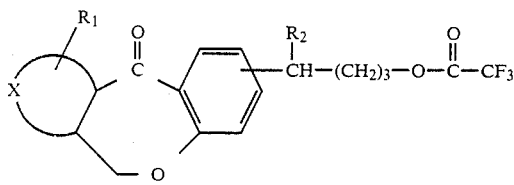

said method comprising reacting a compound of the formula

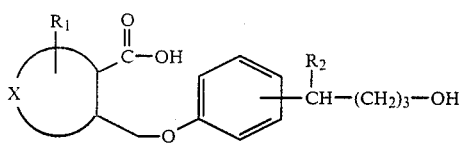

with trifluoroacetic anhydride in solution at a temperature up to the reflux temperature of the reaction mixture; where X together with the carbon atoms to which it is attached is a thiophene ring; where $R_1$ is hydrogen, a straight chain or branched chain alkyl group having 1 to 5 carbon atoms or a halogen atom; and $R_2$ is hydrogen or a straight chain alkyl group having 1 to 5 carbon atoms.

20. Method according to claim 19 wherein the compound of formula (III) is reacted with about 2 to about 2.5 equivalents of trifluoroacetic anhydride in a solvent selected from the group consisting of dichloromethane and chloroform.

21. Method according to claim 19 wherein $R_1$ and $R_2$ are each hydrogen.

22. A method for preparing a compound of the formula

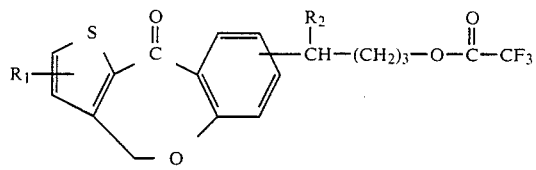

where $R_1$ is hydrogen and a straight chain or branched chain alkyl group having 1 to 5 carbon atoms and $R_2$ is hydrogen or a straight chain alkyl group having 1 to 5 carbon atoms, said method comprising reacting a compound of the formula

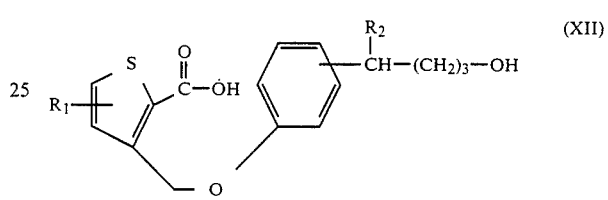

with trifluoroacetic anhydride in solution at a temperature up to the reflux temperature of the reaction mixture.

23. Method according to claim 22 wherein the compound of formula (XII) is reacted with about 2 to about 2.5 equivalents of trifluoroacetic anhydride in a solvent selected from the group consisting of dichloromethane and chloroform.

24. Method according to claim 23 wherein $R_1$ and $R_2$ are each hydrogen.

25. A method for preparing a compound of the formula

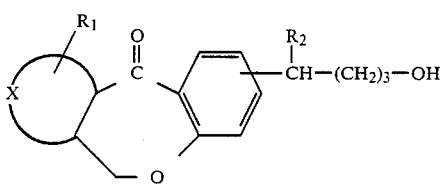

said method comprising hydrolyzing a compound of the formula

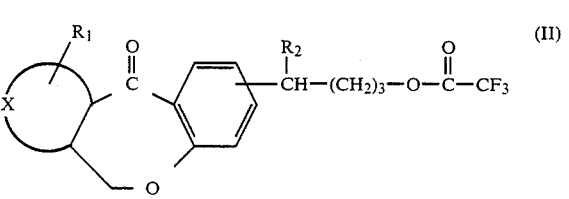

in acidic solution at a temperature up to the reflux temperature of the solvent employed in the solution; where X together with the carbon atoms to which it is attached is a thiophene ring; $R_1$ is hydrogen, a straight chain or branched chain alkyl group having 1 to 5 carbon atoms; and $R_2$ is hydrogen or a straight chain alkyl group having 1 to 5 carbon atoms.

26. Method according to claim 25 wherein the compound of formula (II) is reacted with sulfuric acid or hydrochloric acid and the solvent is selected from the group consisting of acetone, methyl ethyl ketone, methanol, ethanol or propanol.

27. Method of claim 26 wherein the acid is hydrochloric acid and the solvent is acetone.

28. Method according to claim 26 wherein $R_1$ and $R_2$ are each hydrogen.

29. A method for preparing a compound of the formula

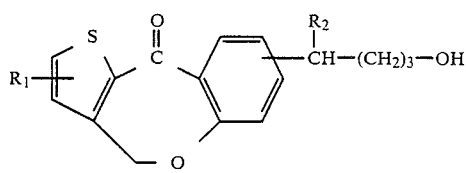

said method comprising hydrolyzing a compound of the formula

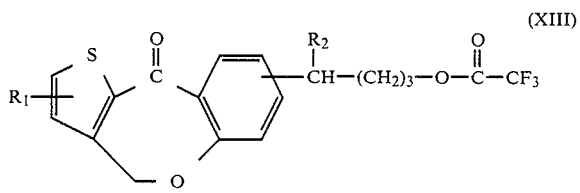

in acidic solution at a temperature up to the reflux temperature of the solvent employed in the solution; where $R_1$ is hydrogen and a straight chain or branched chain alkyl group having 1 to 5 carbon atoms.

30. Method according to claim 29 wherein the compound of formula (XIII) is reaction with sulfuric acid or hydrochloric acid and the solvent is selected from the group consisting of acetone, methyl ethyl ketone, methanol, ethanol or propanol.

31. Method according to claim 30 wherein the acid is hydrochloric acid and the solvent is acetone.

32. Method according to claim 31 wherein $R_1$ and $R_2$ are each hydrogen.

33. A method of alleviating pain in a mammal by administering to a mammal a pain-alleviating effective amount of a compound having long duration of action and low ulcerogenicity, wherein said compound has the formula

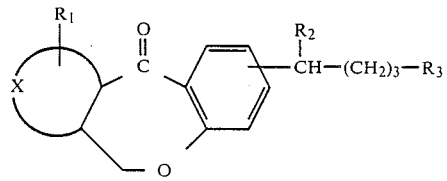

where X together with the carbon atoms to which it is attached is a thiophene ring;
$R_1$ is hydrogen, a straight or branched chain alkyl group having 1 to 5 carbon atoms or a halogen atom;
$R_2$ is hydrogen or a straight chain alkyl group having 1 to 5 carbon atoms; and
$R_3$ is hydroxyl or

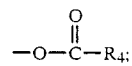

where $R_4$ is straight chain or branched chain alkyl group having 1 to 10 carbon atoms, a phenyl group or a trifluoromethyl group.

34. A method according to claim 33 wherein said compound has the formula

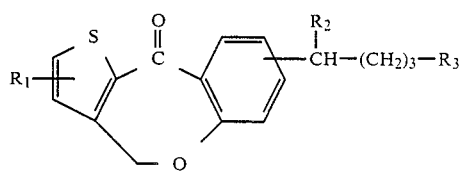

where $R_1$ is hydrogen and a straight chain or branched chain alkyl group having 1 to 5 carbon atoms and $R_2$ is hydrogen and a straight chain alkyl group having 1 to 5 carbon atoms; and $R_3$ is —OH or

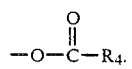

35. A method according to claim 34 wherein $R_3$ is

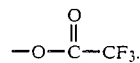

36. A method according to claim 35 wherein $R_1$ and $R_2$ are each hydrogen.

37. A method according to claim 34 wherein $R_3$ is —OH.

38. A method according to claim 37 wherein $R_1$ and $R_2$ are each hydrogen.

39. A method of alleviating inflammation in a mammal by administering to a mammal an inflammation-alleviating effective amount of a compound having long duration of action and low ulcerogenicity, wherein said compound has the formula

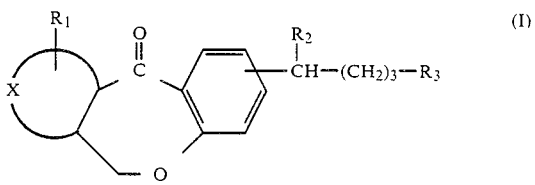

where X together with the carbon atoms to which it is attached is a thiophene ring;
$R_1$ is hydrogen, a straight or branched chain akyl group having 1 to 5 carbon atoms or halogen atom;
$R_2$ is hydrogen or a straight chain alkyl group having 1 to 5 carbon atoms; and
$R_3$ is hydroxyl or

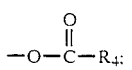

where $R_4$ is a straight chain or branched chain alkyl group having 1 to 10 carbon atoms, a phenyl group or a trifluoromethyl group.

40. A method according to claim 39, wherein said compound has the formula

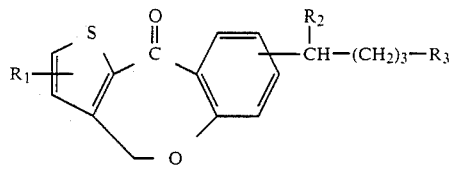

where $R_1$ is hydrogen and a straight or branched chain alkyl group having 1 to 5 carbon atoms; and $R_3$ is —OH or

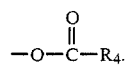

41. A method according to claim 40 wherein $R_3$ is

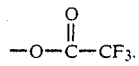

42. A method according to claim 41 wherein $R_1$ and $R_2$ are each hydrogen.

43. A method according to claim 40 wherein $R_3$ is —OH.

44. A method according to claim 43 wherein $R_1$ and $R_2$ are each hydrogen.

45. An antiinflammatory composition comprising an antiinflammatory effective amount of a compound according to claim 1 and a pharmaceutically acceptable carrier therefor.

46. An analgesic composition comprising a pain alleviating effective amount of a compound according to claim 1 and a pharmaceutically acceptable carrier therefor.

47. A compound of the formula

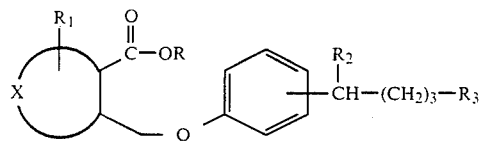

where X together with the carbon atoms to which it is attached is a thiophene ring; R is hydrogen or straight chain or branched alkyl of 1 to 5 carbon atoms; $R_1$ is hydrogen, or a straight chain alkyl group having 1 to 5 carbon atoms; $R_2$ is hydrogen or a straight chain alkyl group having 1 to 5 carbon atoms; and $R_3$ is —OH or

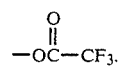

48. An antiinflammatory pharmaceutical composition which comprises an antiinflammatory effective amount of 4-(4,10-dihydro-10-oxothieno [3,2c] [1]-benzoxepin-8-yl)-butanol and a pharmaceutically acceptable carrier therefor.

49. A method of alleviating pain in a mammal by administering to a mammal a pain-alleviating effective amount of 4-(4,10-dihydro-10-oxothieno[3,2-c] [1]benzoxepin-8-yl)-butanol.

50. A method of alleviating inflammation in a mammal by administering to a mammal an inflammation-alleviating effective amount of 4-(4,10-dihydro-10-oxothieno[3,2- c] [1]benzoxepin-8-yl)-butanol.

51. An analgesic pharmaceutical composition which comprises a pain alleviating effective amount of 4-(4,10-dihydro-10-oxothieno[3,2-c] [1]-benzoxepin-8-yl)-butanol and a pharmaceutically acceptable carrier therefor.

* * * * *

UNITED STATES PATENT AND TRADEMARK OFFICE
CERTIFICATE OF CORRECTION

PATENT NO. : 4,496,580

DATED : January 29, 1985

INVENTOR(S) : Lawrence L. Martin and Linda L. Setescak

It is certified that error appears in the above-identified patent and that said Letters Patent is hereby corrected as shown below:

Column 1  Line 64

"substutuent"  should be  -- substituent --

Column 2  Line 65

"Stll"  should be  -- Still --

Column 2  Line 65

"futher"  should be  -- further --

Column 3  Line 57

"respecticely"  should be  -- respectively --

Column 6  Line 14

"cyclizaton"  should be  -- cyclization --

UNITED STATES PATENT AND TRADEMARK OFFICE
CERTIFICATE OF CORRECTION

PATENT NO. :   4,496,580
DATED      :   January 29, 1985
INVENTOR(S) :  Lawrence L. Martin and Linda L. Setescak It is certified that error appears in the above-identified patent and that said Letters Patent is hereby corrected as shown below:

Column 6  Line 15

"acylaton"  should be  -- acylation --

Column 7  Line 60

"ativity"  should be  -- activity --

Column 10  Line 66

"benoxepin"  should be  -- benzoxepin --

Column 16  Line 59

"akyl"  should be  -- alkyl --

Signed and Sealed this

Twenty-third Day of July 1985

[SEAL]

Attest:

DONALD J. QUIGG

Attesting Officer    Acting Commissioner of Patents and Trademarks